US00PP29010P3

(12) United States Plant Patent
Ohde

(10) Patent No.: US PP29,010 P3
(45) Date of Patent: Feb. 27, 2018

(54) ***LIPPIA* PLANT NAMED 'ECOLOPIA2'**

(50) Latin Name: ***Lippia canescens*×*Lippia nodiflora***
Varietal Denomination: ECOLOPIA2

(71) Applicant: Masataka Ohde, Oyama (JP)

(72) Inventor: Masataka Ohde, Oyama (JP)

( * ) Notice: Subject to any disclaimer, the term of this patent is extended or adjusted under 35 U.S.C. 154(b) by 11 days.

(21) Appl. No.: 14/999,180

(22) Filed: Apr. 8, 2016

(65) Prior Publication Data

US 2017/0295688 P1 Oct. 12, 2017

(51) Int. Cl.
*A01H 5/02* (2006.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Keith O Robinson
(74) *Attorney, Agent, or Firm* — Cassandra Bright

(57) ABSTRACT

A new and distinct *Lippia* cultivar named 'ECOLOPIA2' is disclosed, characterized by tolerance to humidity and disease, tall height and large leaf size. Flowers are uniquely light purple The new variety is a *Lippia*, useful for a variety of horticultural purposes.

4 Drawing Sheets

Latin name of the genus and species: *Lippia canescens*× *Lippia nodiflora.*

Variety denomination: 'ECOLOPIA2'.

BACKGROUND OF THE INVENTION

The new *Lippia* cultivar is a product of a planned breeding program conducted by the inventor, Masataka Ohde, in Oyama, Japan. The objective of the breeding program was to produce new *Lippia* varieties for ornamental commercial applications. The cross resulting in this new variety was made during May 2008.

The seed parent is *Lippia canescens* 'Campanga Verde' U.S. Plant Pat. No. 20,120. The pollen parent is an unpatented, unnamed *Lippia nodiflora*. The new variety was discovered on Jul. 1, 2010 by the inventor in a group of seedlings resulting from the 2008 crossing, in a research greenhouse in Oyama, Japan.

Asexual reproduction of the new cultivar 'ECOLOPIA2' was first performed at a commercial greenhouse in Oyama, Japan by terminal vegetative cuttings on Jun. 4, 2010. More than 3 generations have been reproduced by vegetative cuttings. Subsequently, propagation has also shown that the unique features of this cultivar are stable and reproduced true to type.

SUMMARY OF THE INVENTION

The cultivar 'ECOLOPIA2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ECOLOPIA2'. These characteristics in combination distinguish 'ECOLOPIA2' as a new and distinct *Lippia* cultivar:

1. Light purple flower color.
2. Tolerance to disease.

3. Tolerance to high humidity.
4. Above average height.
5. Above average leaf size.
6. Large inflorescence diameter.
7. Variety is sterile.

PARENT COMPARISON

Plants of the new cultivar 'ECOLOPIA2' are similar to the pollen parent in most horticultural characteristics. The new variety however differs in the following characteristics:

1. Taller plant height, measured at foliar plane; the pollen parent grows to 4 cm, the new variety to 5 cm.
2. Leaves of the new variety are more rounded obovate.
3. The new variety has a better tolerance for disease.
4. Corolla color of the pollen parent is Purple 76B, corolla color of 'ECOLOPIA2' is Purple 75B.

Plants of the new cultivar 'ECOLOPIA2' are similar to the seed parent, *Lippia* 'Campagna Verde' U.S. Plant Pat. No. 20,120 in most horticultural characteristics. The new variety however differs in the following characteristics:

1. Taller plant height, measured at foliar plane. 'Campagna Verde' grows to 3 cm, the new variety to 5 cm.
2. Larger inflorescence diameter: 'Campagna Verde' typically 0.7 cm, 'ECOLOPIA2' typically 1.3 cm.
3. Stronger tolerance to disease under high heat and high humidity conditions.
4. Corolla color of 'Campagna Verde' is Violet-Blue 91D, corolla color of 'ECOLOPIA2' is Purple 75B.
5. Leaf blade shape of 'ECOLOPIA2' leaf blade is more rounded obovate.

COMMERCIAL COMPARISON

'ECOLOPIA2' can be compared to the unpatented, unnamed commercial *Lippia nodiflora*. Plants of *Lippia nodiflora* are similar to plants of 'ECOLOPIA2' in most horticultural characteristics. However 'ECOLOPIA2' differs from *Lippia nodiflora* in the following characteristics:

1. The new variety is observed sterile. The comparator produces many seeds.
2. Greater cold tolerance.
3. The new variety produces purple inflorescence, this comparator has white inflorescence.

BRIEF DESCRIPTION OF THE PHOTOGRAPHS

The accompanying photograph in FIG. 1 illustrates in full color typical flowers and foliage of a plant of 'ECOLOPIA2' grown outdoors in Oyama, Japan.

Figure 1:
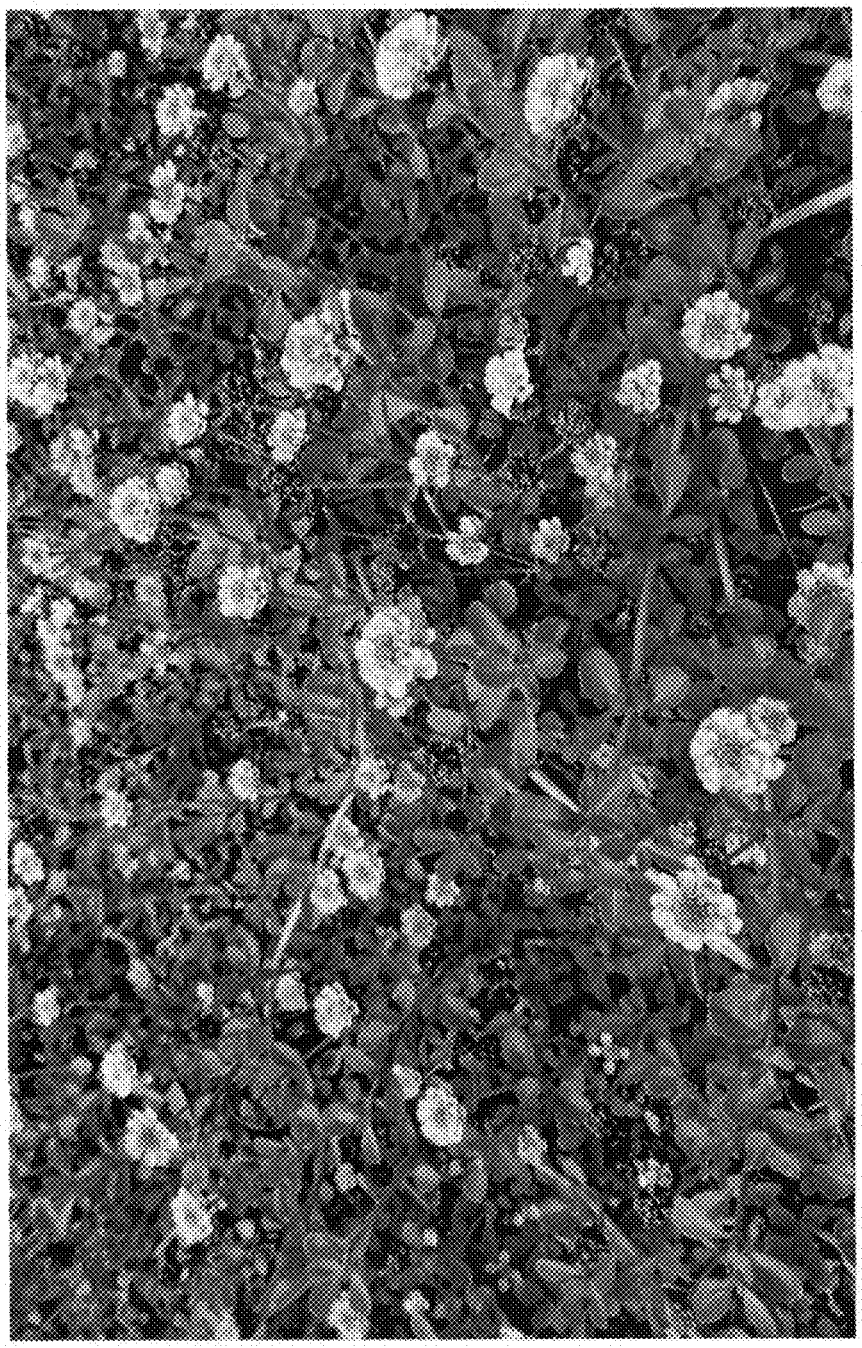
Figure 2:
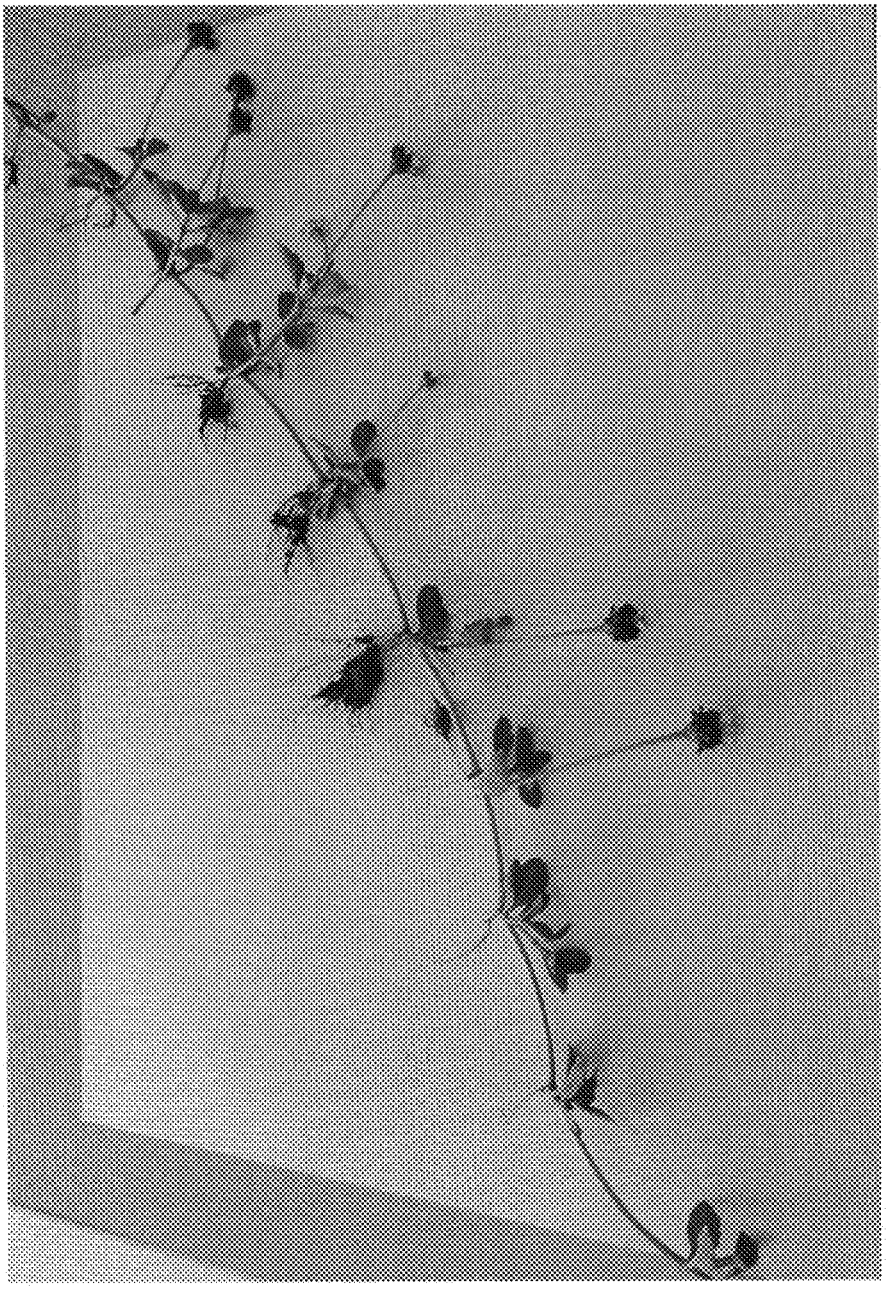
FIG. 2 illustrates a rooted stem with inflorescence.
Figure 3:
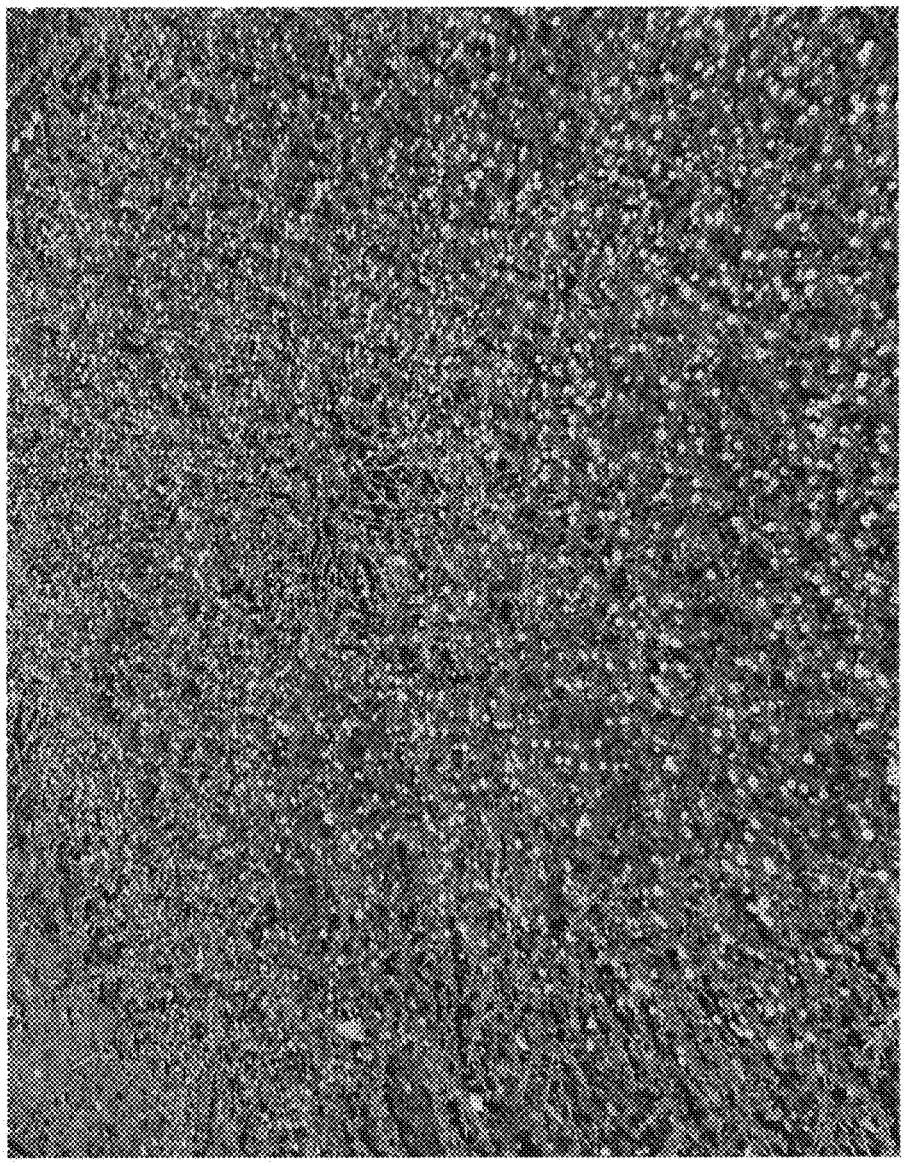
FIG. 3 illustrates a mass planting view of the plant grown outdoors.
Figure 4:
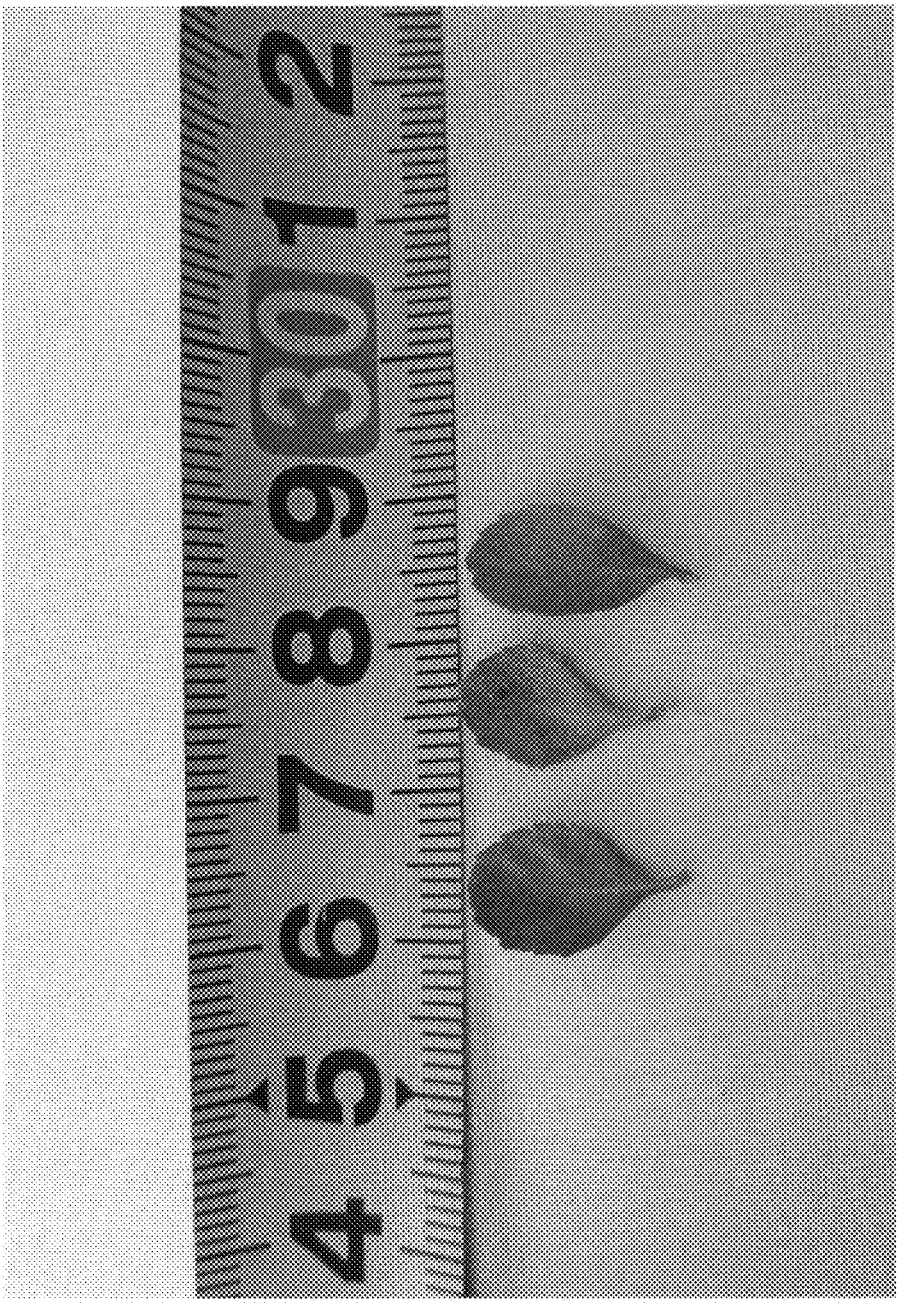

FIG. 4 is a comparison of foliage. Foliage of 'ECOLOPIA2' is farthest left in the photo. The center leaf in the photo is the seed parent foliage, farthest right is the pollen parent foliage.

Plants are typically grown as ground cover, the plants illustrated are planted directly in the ground. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'ECOLOPIA2' plants grown both outdoors and in a temperature controlled greenhouse in Oyama, Japan. Temperatures ranged from −7° C. to 25° C. at night to 3° C. to 50° C. during the day. No artificial light, photoperiodic treatments were given to the plants. Plants were grown both outside research field with plowed soil supplemented with fertilizer containing 8% N, 8% P, and 8% K, and in temperature-controlled and uncontrolled greenhouses in a mixture of Kanuma soil, peat and vermiculite supplemented with the same fertilizer. Measurements and numerical values represent averages of typical plant types.

Botanical classification: *Lippia canescens*×*nodiflora* 'ECOLOPIA2'.

PROPAGATION

Time to initiate roots: 3 to 7 days at approximately 23° C.

Root description: Thin root stretching to downward reaching as deep as 3 feet or deeper with sandy soil.

PLANT

Age of plant described: Approximately 90 days from rooted cutting.

Time of year: July 2014.

Growth habit: Creeping, creating a dense mat.

Planting description: Not in a pot, planted in the ground outside of greenhouse.

Height: 4 to 5 cm.

Plant spread: 136 cm diameter, maximum in a year.

Growth rate: Vigorous.

Branching characteristics: Dense.

Length of primary lateral branches: 68 cm.

Diameter of lateral branches: 5 mm.

Quantity of primary lateral branches: Many, plant continuously forming branches, approximately 2 to 4 per linear cm.

Characteristics of primary lateral branches:

*Form.*—Round.

*Diameter.*—5 mm.

*Color.*—Near Green 137A. Some flushing Brown 200C.

*Texture.*—Slightly scaly.

*Strength.*—Very strong, difficult to break.

Internode length: 3-4 cm.

FOLIAGE

Leaf:

*Arrangement.*—Opposite.

*Average length.*—1.2 cm.

*Average width.*—0.7 cm.

*Shape of blade.*—Very round obovate

*Apex.*—Broad acute.

*Base.*—Attenuate.

*Margin.*—Crenate.

*Texture of top surface.*—Glabrous.

*Texture of bottom surface.*—Glabrous.

*Aspect.*—Slightly upwardly cupped.

*Color.*—Young foliage upper (front) Near RHS Yellow-Green 146B. Young foliage under (back) side: Near RHS Green 137D. Mature foliage upper side: Near RHS Yellow-Green 146B. Mature foliage under side: Near RHS Green 137D.

*Venation.*—Type: Pinnate. Venation color upper side: Near RHS Green 139D. Venation color under side: Near RHS Green 139D.

*Petiole.*—Leaves sessile.

FLOWER

Natural flowering season: May to October.

Days to flowering from rooted cutting: 1-2 months, depend on temperature and light conditions.

Inflorescence and flower type and habit: Terminal umbel.

Persistent or self-cleaning: Persistent.

Bud:

*Shape.*—Oval.

*Length.*—0.5 cm.

*Diameter.*—0.5 cm.

*Color.*—Near RHS Purple 77A.

Inflorescence:

*Depth.*—4.0 cm.

*Diameter.*—1.8 cm.

*Average quantity of individual flowers per inflorescence.*—55.

Corolla:

*Individual flower.*—

*Depth.*—0.5 cm.

*Diameter.*—0.3 cm.

*Petals/lobes.*—Number: 1 fully formed petal. Length: 0.5 cm. Width: 0.3 cm. Shape: Tube, flaring open at very end. Apex: Blunt round. Base: Fused. Margin: Ruffled at apex. Texture: Glabrous all surfaces. Color: When opening: Upper surface: Near RHS Purple 75B. Lower surface: Near RHS Purple 75B. Fully opened: Upper surface: Near RHS Purple 75B. Lower surface: Near RHS Purple 75B 91D.

*Throat.*—Color: Near RHS Purple 76D Texture: Glabrous.

*Tube*.—Interior Tube color: Near RHS Purple 75B, base near Yellow-Orange 17A. Exterior Tube color: Near RHS Purple 75B. Texture: Glabrous.

Calyx:

*Form*.—Fused into a tube.

*Length*.—0.2 cm.

*Diameter*.—0.2 cm.

*Sepal texture*.—Glabrous.

*Sepal color*.—Upper surface: Near RHS Green 139C. Lower surface: Near RHS Green 139C.

Fragrance: None.

Pedicels: Not present.

Peduncles:

*Length*.—3.0 cm to 5.0 cm.

*Diameter*.—0.1 cm.

*Color*.—Near RHS Green 139C.

*Texture*.—Glabrous.

REPRODUCTIVE ORGANS

Stamens:

*Number* (*per flower*).—4.

*Filament length*.—0.05 cm.

*Anthers*.—Shape: Linear. Length: 0.05 cm. Color: Near RHS Yellow-Orange 17A.

*Pollen*.—Not present.

Pistils:

*Quantity per flower*.—1. Minute, not measurable.

OTHER CHARACTERISTICS

Seeds and fruits: Not observed.

Disease/pest resistance: Excellent resistance to common diseases of *Lippia nodiflora*. New variety has better resistance to disease under humid and hot conditions than parents. The most common pathogens found in *Lippia* are fungus, including *Puccinia* and *Colletrotrichum*. No particular pest resistance observed.

Temperature tolerance: Plant of the new hybrid have shown excellent resistance to high and low temperature extremes, having been grown successfully under temperature conditions ranging from a gentle frost outdoors, just below 0 degrees Celsius, to 50 degrees Celsius in an uncontrolled greenhouse.

Physical durability: New variety has excellent tolerance to be foot traffic.

Soil ph: New variety has excellent tolerance to a range of soil pH from 4.0-12.0.

What is claimed is:

1. A new and distinct cultivar of *Lippia* plant named 'ECOLOPIA2' as herein illustrated and described.

* * * * *